United States Patent
Hoelscher et al.

(10) Patent No.: US 9,457,201 B2
(45) Date of Patent: Oct. 4, 2016

(54) PORTABLE DEVICE TO INITIATE AND MONITOR TREATMENT OF STROKE VICTIMS IN THE FIELD

(71) Applicant: The Regents of the University of California, Oakland, CA (US)

(72) Inventors: Thilo Hoelscher, San Diego, CA (US); Arne Voie, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 46 days.

(21) Appl. No.: 13/892,187

(22) Filed: May 10, 2013

(65) Prior Publication Data

US 2014/0155788 A1    Jun. 5, 2014

Related U.S. Application Data (60) Provisional application No. 61/646,106, filed on May 11, 2012, provisional application No. 61/681,025, filed on Aug. 8, 2012.

(51) Int. Cl.
*A61N 7/00* (2006.01)
*A61B 8/08* (2006.01)
(Continued)

(52) U.S. Cl.
CPC ............... *A61N 7/00* (2013.01); *A61B 8/0808* (2013.01); *A61B 8/481* (2013.01);
(Continued)

(58) Field of Classification Search
CPC .......... A61N 7/00; A61N 2007/0039; A61N 2007/0052; A61N 2007/0078; A61B 8/0808; A61B 8/481; A61B 8/0802; A61B 2017/22008; A61H 2201/105; A61H 2201/0176; A61H 2201/5005; A61H 2201/5097; A61H 2201/5043; A61H 2201/5002; A61H 2201/1604; A61H 2201/5058; A61H 2201/018; A61H 2205/02; A61H 23/0245
USPC ........................................................ 601/2
See application file for complete search history.

(56) References Cited

U.S. PATENT DOCUMENTS 5,601,526 A  2/1997  Chapelon et al.
6,196,972 B1 * 3/2001  Moehring ................. 600/454
(Continued)

FOREIGN PATENT DOCUMENTS

WO   02/15803 A1    2/2002
WO   2011/027264 A1  3/2011
WO   2011/082408 A2  7/2011

OTHER PUBLICATIONS

Hölscher T, Schlachetzki F, Zimmermann M, Jakob W, Ittner KP, Haslberger J, Bogdahn U, Boy S: Transcranial Ultrasound from Diagnosis to Early Stroke Treatment Part I: Feasibility of Prehospital Cerebrovascular Assessment. Cerebrovascular Diseases, 26: 659-663, 2008.

(Continued)

*Primary Examiner* — Long V Le
*Assistant Examiner* — Angela M Hoffa
(74) *Attorney, Agent, or Firm* — Mark D. Wieczorek; Mayer & Williams, PC (57) ABSTRACT

Methods and apparatuses are provided for initiating stroke treatment "in the field" and/or during the transport of the patient to a care facility. The capability is provided to adjust automatically to the individual "therapeutic window" for each single patient, which is crucial because of the significant differences in skull morphology between humans of different age, gender and race. Further, the methods and apparatuses are based on the use of non-invasive application of ultrasound, as well as the non-invasive application of ultrasound in combination with an acoustically active agent, such as microbubbles, where stable cavitation of the microbubbles caused by the ultrasound may be relied upon as an underlying mechanism for both the therapeutic application as well as its control.

11 Claims, 6 Drawing Sheets

(51) Int. Cl.
  A61B 17/22    (2006.01)
  A61H 23/02    (2006.01)
(52) U.S. Cl.
  CPC ..... A61B 2017/22008 (2013.01); A61H 23/0245
      (2013.01); A61H 2201/018 (2013.01); A61H
          2201/0176 (2013.01); A61H 2201/105
      (2013.01); A61H 2201/1604 (2013.01); A61H
          2201/5002 (2013.01); A61H 2201/5005
      (2013.01); A61H 2201/5043 (2013.01); A61H
          2201/5058 (2013.01); A61H 2201/5097
      (2013.01); A61H 2205/02 (2013.01); A61N
          2007/0039 (2013.01); A61N 2007/0052
          (2013.01); A61N 2007/0078 (2013.01)

(56)  References Cited

U.S. PATENT DOCUMENTS

| | | | |
|---|---|---|---|
| 6,398,772 | B1 * | 6/2002 | Bond et al. ............. 604/507 |
| 6,468,219 | B1 * | 10/2002 | Njemanze ............. 600/454 |
| 6,635,017 | B1 * | 10/2003 | Moehring et al. ....... 600/437 |
| 6,682,483 | B1 * | 1/2004 | Abend et al. ........... 600/437 |
| 6,682,502 | B2 * | 1/2004 | Bond et al. ............. 604/22 |
| 6,945,937 | B2 * | 9/2005 | Culp et al. ............. 600/437 |
| 7,037,267 | B1 * | 5/2006 | Lipson et al. ........... 600/454 |
| 7,300,414 | B1 | 11/2007 | Holland et al. |
| 7,425,198 | B2 * | 9/2008 | Moehring et al. ....... 600/454 |
| RE42,803 | E * | 10/2011 | Lipson et al. ........... 600/454 |
| 8,211,023 | B2 * | 7/2012 | Swan et al. ............. 600/457 |
| 8,679,051 | B2 * | 3/2014 | Keenan et al. .......... 604/24 |
| 2002/0198469 | A1 * | 12/2002 | Bridger et al. .......... 600/586 |
| 2004/0049134 | A1 | 3/2004 | Tosaya et al. |
| 2004/0138563 | A1 * | 7/2004 | Moehring et al. ....... 600/439 |
| 2007/0083120 | A1 * | 4/2007 | Cain et al. ............. 600/439 |
| 2007/0167765 | A1 * | 7/2007 | Unger et al. ........... 600/437 |
| 2008/0033297 | A1 | 2/2008 | Sliwa |
| 2008/0262350 | A1 * | 10/2008 | Unger ................. 600/439 |
| 2009/0099482 | A1 | 4/2009 | Furuhata et al. |
| 2010/0056924 | A1 | 3/2010 | Powers |
| 2010/0160779 | A1 * | 6/2010 | Browning et al. ....... 600/439 |
| 2010/0160780 | A1 * | 6/2010 | Swan et al. ............. 600/439 |
| 2010/0210940 | A1 * | 8/2010 | Bradley et al. .......... 600/427 |
| 2011/0112394 | A1 | 5/2011 | Mishelevich |
| 2012/0083717 | A1 | 4/2012 | Alleman et al. |
| 2012/0083718 | A1 | 4/2012 | Alleman et al. |
| 2012/0165670 | A1 * | 6/2012 | Shi et al. ............. 600/442 |

OTHER PUBLICATIONS

Schlachetzki F, Herzberg M, Hölscher T, Ertl M, Zimmermann M, Pels H, Bogdahn, Boy S: Transcranial Ultrasound from Diagnosis to Early Treatment. Part II: Prehospital Neurosonography in Patients with Acute Stroke—The Regensburg Stroke Mobile Project. Cerebrovascular Diseases 2012, 33: 262-271.

Hölscher T, Raman R, Ernstrom K, Perrish J, Le DT, Lyden P, Mattrey R: In Vitro Sonothrombolysis With Duplex Ultrasound: First Results Using a Simplified Model Cerebrovascular Diseases, 28(4): 365-370, 2009.

Hölscher T, Fisher D, Raman R, Ernstrom K, Zadicario, Bradley WG, Voie A: Noninvasive Transcranial Clot Lysis Using High Intensity Focused Ultrasound. Journal of Neurology and Neurophysiology 2011, S1-002.

Hölscher T, Raman R, Fisher D, Ahadi G, Zadicario E, Voie A: Effects of Varying Duty Cycle and Pulse Width on High Intensity Focused Ultrasound (HIFU) Induced Transcranial Thrombolysis. Ultrasound in Medicine and Biology (in review), 2011.

Hölscher T, Fisher D, Voie A: Introduction of a Rabbit Carotid Artery Model for Sonothrombolysis Research. Translational Stroke Research (in review), 2011.

Ahadi G, Welch C, Fisher D, Raman R, Ernstrom K, Grimm M, Voie A, Hölscher T: Transcranial Sonothrombolysis Using High Intensity Focused Ultrasound: Impact of Increasing Output Power on Clot Weight Loss and Clot Fragmentation. Ultrasound in Medicine and Biology (in review), 2011.

Voie A, Fisher D, Hölscher T: Transcranial Measurements of the Acoustic Field Produced by a Low Frequency Focused Ultrasound System. Ultrasound in Medicine and Biology (in review), 2011.

Hölscher T: Prehospital Stroke Diagnosis and Treatment in Ambulances and Emergency Helicopters: Fiction or Future ? Annals of Emergency Medicine (submitted), 2011.

Alexandrov AV, Molina CA, Grotta JC, et al. Ultrasound-enhanced systemic thrombolysis for acute ischemic stroke. N Engl J Med. 2004;351(21):2170-2178.

Eggers J, Koch B, Meyer K, Konig I, Seidel G. Effect of ultrasound on thrombolysis of middle cerebral artery occlusion. Ann Neurol. 2003;53(6):797-800.

Eggers J, Konig IR, Koch B, Handler G, Seidel G. Sonothrombolysis with transcranial color-coded sonography and recombinant tissue-type plasminogen activator in acute middle cerebral artery main stem occlusion: results from a randomized study. Stroke. 2008;39(5):1470-1475.

Braaten JV, Goss RA, Francis CW. Ultrasound reversibly disaggregates fibrin fibers. Thromb Haemost. 1997;78(3):1063-1068.

Devcic-Kuhar B, Pfaffenberger S, Gherardini L, et al. Ultrasound affects distribution of plasminogen and tissuetype plasminogen activator in whole blood clots in vitro. Thromb Haemost. 2004;92(5):980-985.

Datta S, Coussios CC, McAdory LE, et al. Correlation of cavitation with ultrasound enhancement of thrombolysis. Ultrasound Med Biol. 2006;32(8):1257-1267.

Datta S, Ammi A.Y., Coussios C.C., Holland, C.K. Monitoring and simulating stable cavitation during ultrasound-enhanced thrombolysis. Journal of the Acoustic Society of America. 2007;122(3052).

Prokop AF, Soltani A, Roy RA. Cavitational mechanisms in ultrasound-accelerated fibrinolysis. Ultrasound Med Biol. 2007;33(6):924-933.

Datta S, Coussios CC, Ammi AY, Mast TD, de Courten-Myers GM, Holland CK. Ultrasound-enhanced thrombolysis using definity((r)) as a cavitation nucleation agent. Ultrasound Med Biol. 2008;34(9):1421-1433.

Siegel RJ, Atar S, Fishbein MC, et al. Noninvasive, transthoracic, low-frequency ultrasound augments thrombolysis in a canine model of acute myocardial infarction. Circulation. 2000;101(17):2026-2029.

Siegel RJ, Atar S, Fishbein MC, et al. Noninvasive transcutaneous low frequency ultrasound enhances thrombolysis in peripheral and coronary arteries. Echocardiography. 2001;18(3):247-257.

Nedelmann M, Brandt C, Schneider F, et al. Ultrasound-induced blood clot dissolution without a thrombolytic drug is more effective with lower frequencies. Cerebrovasc Dis. 2005;20(1):18-22.

Nedelmann M, Eicke BM, Nolle F, Lierke EG, Kempski O. [The ultrasound contrast medium levovist increases the thrombolytic effect of low frequency ultrasound]. Med Klin (Munich). 2002;97(4):216-220.

Francis CW, Suchkova VN. Ultrasound and thrombolysis. Vasc Med. 2001;6(3):181-187.

Daffertshofer M, Gass A, Ringleb P, et al. Transcranial low-frequency ultrasound-mediated thrombolysis in brain ischemia: increased risk of hemorrhage with combined ultrasound and tissue plasminogen activator: results of a phase II clinical trial. Stroke. 2005;36(7):1441-1446.

Daffertshofer M, Huang Z, Fatar M, et al. Efficacy of sonothrombolysis in a rat model of embolic ischemic stroke. Neurosci Lett. 2004;361(1-3):115-119.

Pfaffenberger S, Devcic-Kuhar B, El-Rabadi K, et al. 2MHz ultrasound enhances t-PA-mediated thrombolysis: comparison of continuous versus pulsed ultrasound and standing versus travelling acoustic waves. Thromb Haemost. 2003;89(3):583-589.

Alexandrov AV. Ultrasound-enhanced thrombolysis for stroke: clinical significance. Eur J Ultrasound. 2002;16 (1-2):131-140.

Cintas P, Nguyen F, Boneu B, Larrue V. Enhancement of enzymatic fibrinolysis with 2-MHz ultrasound and microbubbles. J Thromb Haemost. 2004;2(7):1163-1166.

(56) References Cited

OTHER PUBLICATIONS

Everbach EC, Francis CW. Cavitational mechanisms in ultrasound-accelerated thrombolysis at 1 MHz. Ultrasound Med Biol. 2000;26(7):1153-1160.
Pfaffenberger S, Devcic-Kuhar B, Kollmann C, et al. Can a commercial diagnostic ultrasound device accelerate thrombolysis? An in vitro skull model. Stroke. 2005;36(1):124-128.
Molina CA, Ribo M, Rubiera M, et al. Microbubble administration accelerates clot lysis during continuous 2-MHz ultrasound monitoring in stroke patients treated with intravenous tissue plasminogen activator. Stroke. 2006;37(2):425-429.
Mizushige K, Kondo I, Ohmori K, Hirao K, Matsuo H. Enhancement of ultrasound-accelerated thrombolysis by echo contrast agents: dependence on microbubble structure. Ultrasound Med Biol. 1999;25(9):1431-1437.
Tachibana K, Tachibana S. Albumin microbubble echo-contrast material as an enhancer for ultrasound accelerated thrombolysis. Circulation. 1995;92(5):1148-1150.
Wu Y, Unger EC, McCreery TP, et al. Binding and lysing of blood clots using MRX-408. Invest Radiol, Dec. 1998, pp. 880-885.
International Preliminary Report on Patentability mailed Nov. 20, 2014, issued in connection with corresponding International Application No. PCT/US13/040664 (14 pages total).
Extended European Search Report mailed Jul. 13, 2015, issued in connection with corresponding European Application No. 13787955.7 (8 pages total).
International Search Report mailed Sep. 6, 2013, issued in connection with corresponding International Application No. PCT/US13/040664 (4 pages total).
First Examination Report mailed Nov. 1, 2015, issued in connection with corresponding Australian Application No. 2013259194 (3 pages total).
Patent Examination Report mailed Nov. 1, 2015, issued in connection with corresponding Australian Application No. 2013259194 (3 pages total).

* cited by examiner

PORTABLE DEVICE TO INITIATE AND MONITOR TREATMENT OF STROKE VICTIMS IN THE FIELD

CROSS-REFERENCE TO RELATED APPLICATIONS

This application claims benefit of priority to U.S. Provisional Patent Application Ser. No. 61/681,025, filed Aug. 8, 2012, entitled "PORTABLE DEVICE TO INITIATE AND MONITOR STROKE VICTIMS IN THE FIELD" and U.S. Provisional Patent Application Ser. No. 61/646,106, filed May 11, 2012, entitled "METHOD AND PORTABLE APPARATUS FOR TREATING STROKE VICTIMS IN THE FIELD", owned by the assignee of the present application and herein incorporated by reference in its entirety.

GOVERNMENT FUNDING

This invention was made with government support under HL091043 awarded by the National Institute of Health. The government has certain rights in the invention.

TECHNICAL FIELD

The present invention relates to treating victims of stroke or stroke-like events, and in particular, to providing a portable device to initiate treatment and monitor victims "in the field" and/or during transport to a care facility by applying ultrasound non-invasively, as well as in combination with intravenously administered microbubbles, through an intact skull.

BACKGROUND

A stroke or cerebrovascular accident (CVA) refers to a rapid loss of brain function due to a disturbance in the brain's blood supply, for example, due to a lack of blood flow (referred to as ischemia) caused by blockage, e.g., thrombosis or arterial embolism, or a hemorrhage. Stroke is the second leading cause of death worldwide and the third leading cause of death in the United States, between cardiac diseases (the number one worldwide common cause of death) and tumor diseases (the number three worldwide common cause of death). The majority of acute ischemic strokes (80%) are caused by thrombo-embolism, and in comparison to, e.g., cardiac and tumor-related diseases, the amount of acute cell death in ischemic stroke during the initial phase of a stroke event is significantly greater. That is, neuronal brain cells (neurons) are very sensitive to oxygen supply, which may be interrupted, for example, due to a sudden arterial vessel occlusion. Thus, neurons turn into apoptosis within the first 60 seconds of oxygen deprivation. Apoptosis is defined as a programmed cell death, which means that neurons start to die irreversibly even at this very early point in time if recanalization, and therefore providing an oxygen supply, does not occur.

Figure 1:
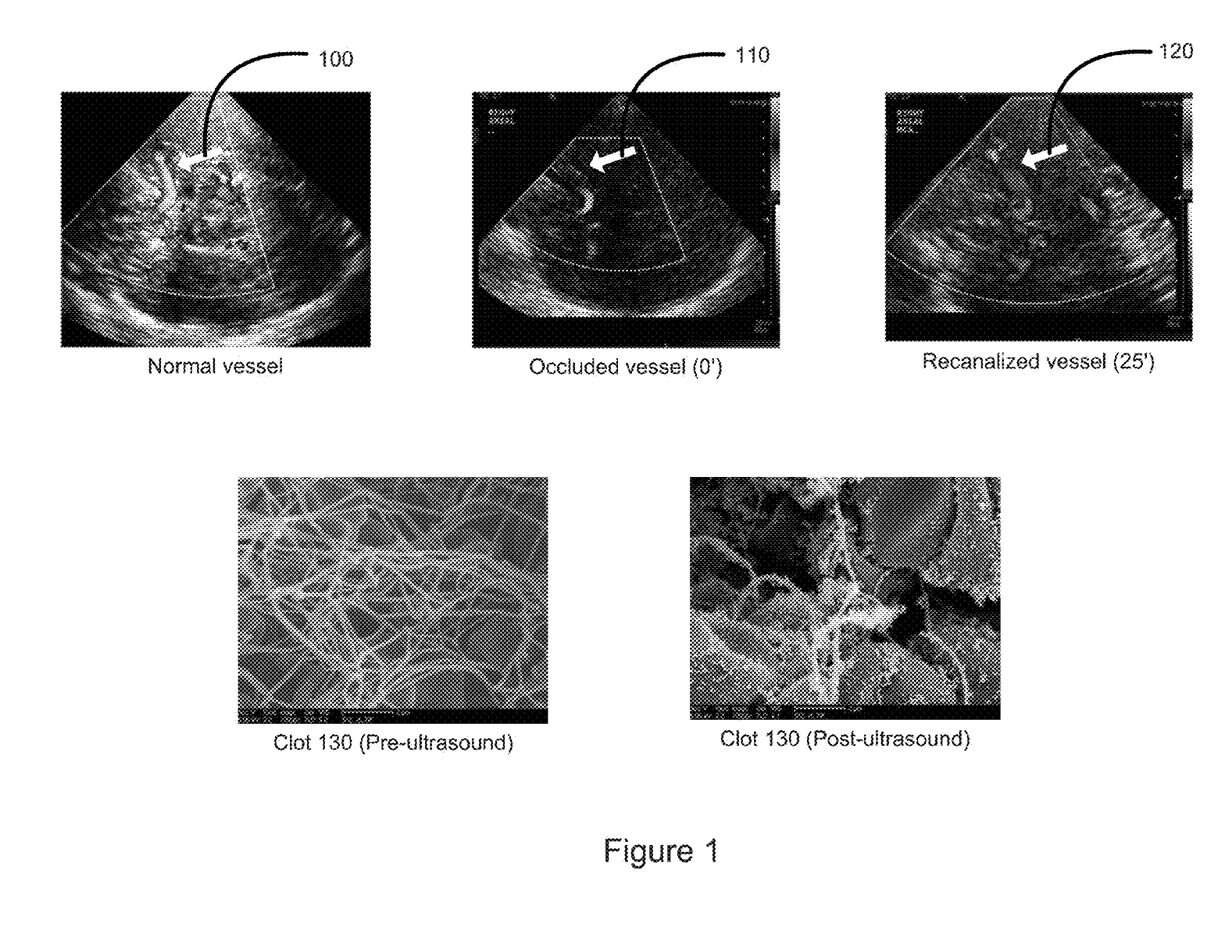
FIG. 1 are illustrations of a normal vessel, an occluded vessel, and a recanalized vessel, and the effects of ultrasound on a blood clot.

FIG. 1 illustrates one example of a normal vessel, indicated by arrow 100, an example of an occluded vessel, indicated by arrow 110, and an example of a recanalized vessel at, e.g., 25 minutes after occlusion, indicated by arrow 120. FIG. 1 further illustrates an example of a blood clot 130, as observed prior to the application of ultrasound treatment, as well as an example of a blood clot 130, as observed post-ultrasound application.

In the case of acute ischemic stroke, it has been shown that an average of 1,900,000 neurons die every minute due to intracranial arterial vessel occlusion. Hence, it is a worldwide, common understanding that therapeutic options to recanalize the affected brain artery should be applied as early as possible. Recent advances in stroke care, such as the installation of specialized Stroke Centers/Units or TeleMedicine concepts, have improved stroke care in selected areas. However, all of these activities are either initiated or coordinated mainly by well-known academic centers in developed countries, and the overall impact of these improvements on stroke care are negligible.

Figure 2:
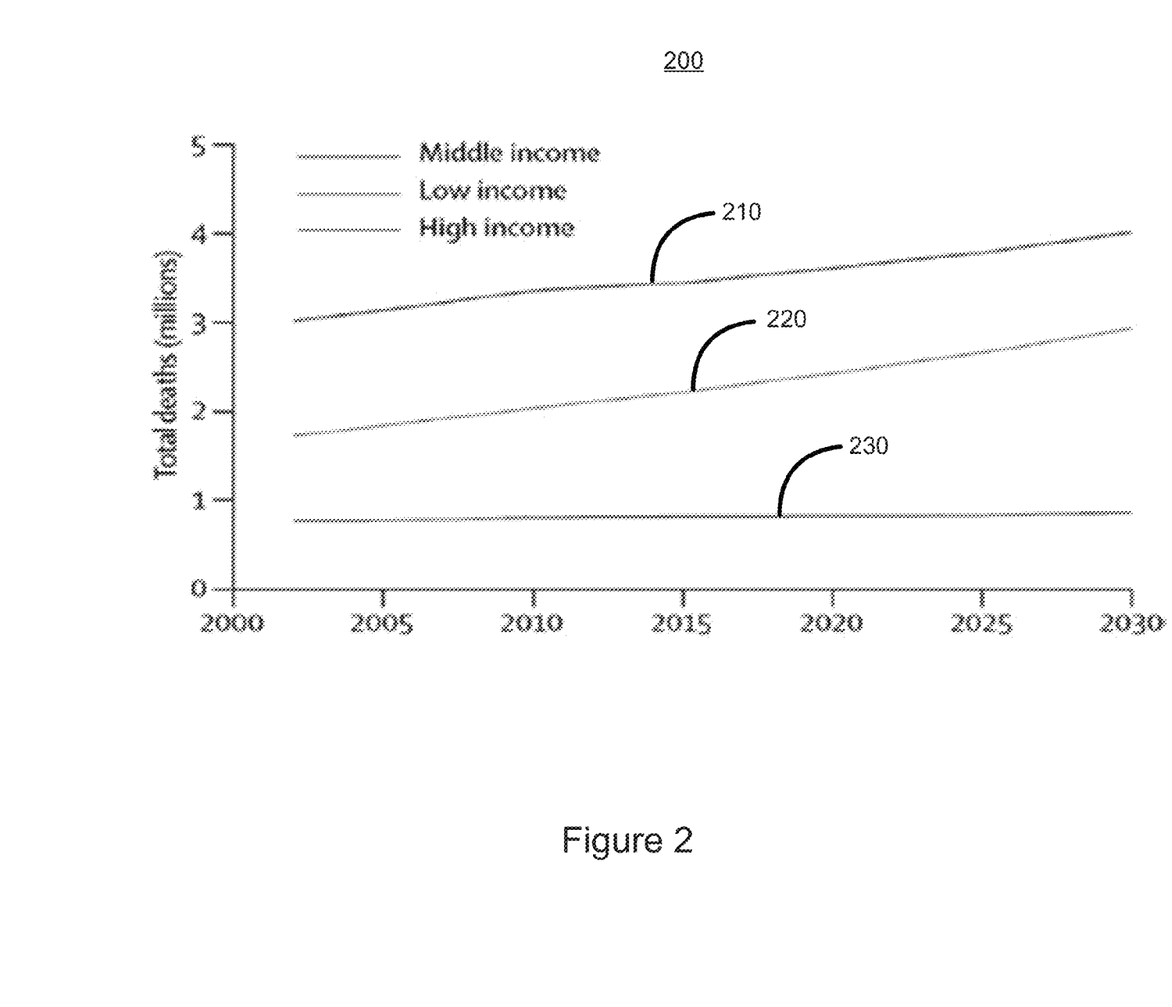
FIG. 2 is a graph illustrating the prevalence of stroke-related deaths among different socio-economic groups.

It should be noted that the cause of the worldwide growing incidence of stroke may be attributed to three main causes. First, there is a lack of public awareness of the disease and its symptoms. Second, all conventional therapeutic interventions require hospitalization of the patient. Third, and among people of all ages, more than 85% of global deaths from stroke occur in either low or middle-income countries, where approximately 85% of the world's total population resides. FIG. 2 illustrates that deaths attributable to stroke in middle income individuals was approximately 3 million in the early 2000s, and is increasing, as indicated by line 210, almost 2 million for low income individuals and also increasing, as indicated by line 220. In contrast, and as indicated by line 230, deaths attributable to stroke amongst high income individuals in the early 2000s and projected through 2030 remains under 1 million.

Currently, there is no known therapeutic option which allows the treatment of acute stroke patients to begin "in the field," e.g., at the site of the emergency and/or during transport to a care facility, such as a hospital. In the field treatment can be considered to be of critical importance since the majority of strokes occur in suburban or rural areas, often a great distance from specialized stroke centers. In these cases, the time delay between an emergency call, e.g., 911 call, arrival at the site of the emergency, and transport to the specialized stroke center may often be a limiting factor as to whether a patient survives, suffers from lifelong invalidity, or fully recovers without any deficits.

One recently developed device, which aims to treat stroke victims using ultrasound, is a device, referred to as the CLOTBUST™-ER by Cerevast Therapeutics, Inc. However, the CLOTBUST™-ER ultrasound stroke treatment device has been developed for stroke treatment in an emergency room, after a patient's admission to a hospital, and in combination with Tissue Plasminogen Activator (tPA), currently the only FDA approved lytic drug for stroke treatment. Accordingly, and again, even with such a device, treatment in the field remains lacking for stroke victims.

SUMMARY

Various embodiments of the present invention are directed to methods and devices for initiating stroke treatment "in the field" and/or during the transport of the patient to a care facility. The capability is provided to adjust automatically to the individual "therapeutic window" for each single patient, which is crucial due of the significant differences in skull morphology between humans of different age, gender and race. Further, the methods and devices are based on the combinational use of microbubbles and stable cavitation as an underlying mechanism for both the therapeutic application as well as its control.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION

Various embodiments disclosed herein are directed to methods and apparatuses for treating patients who may suffer from an acute ischemic stroke in the field and/or during transport to a care facility. In accordance with one embodiment, such treatment can be effectuated by applying ultrasound noninvasively, through an intact skull/cranium, to trigger various biophysical effects. In accordance with another embodiment, such noninvasive application of ultrasound can be performed in combination with intravenously administered microbubbles through an intact skull/cranium, to trigger various biophysical effects. Among other effects, the aforementioned biophysical effects triggered in accordance with the utilization of various embodiments may include, but are not limited to the following: a) the improvement of collateral and interstitial flow; b) restoration of arterial flow in an affected vascular supply area; c) reduction of concomitant edema; d) activation of chaperone proteins; e) potential progenitor cell stimulation; and f) the actual lysis of a vessel occluding blood clot.

Ultrasound can be applied in a pulsed manner using a transmit frequency of, e.g., 200 kHz, at which the distortion of an applied ultrasound beam by the skull is negligible. The ultrasound can be applied from, e.g., both sides of a patient's head in an alternating fashion. Applying ultrasound in such a manner can increase the treatment area, as well as avoid in parallel potential side effects, due to the overlay of individual sound fields. In particular, two ultrasound probes/electrodes can be placed in the anatomical area of the temporal bone and close to the ear. The two ultrasound probes can be disposable, and have the capability to transmit an ultrasound beam, as well as receive acoustic signals, caused by ultrasound microbubble induced cavitation events, in accordance with certain embodiments.

In accordance with one embodiment, the pulse width of an applied ultrasound bean may be short (e.g., 100 µs) to allow a high pulse repetition rate (e.g., 5 kHz) to provide sufficient energy deposition. The acoustic output power may be rather low (e.g., 4 W) to accomplish a focal maximum intensity below the Food and Drug Administration (FDA)-suggested limit of 720 mW/cm$^2$. With regard to beam forming, a chirp mode may be utilized, although other embodiments can utilize fundamental or phase inversion modality.

In accordance with another embodiment, and as alluded to previously, ultrasound may also be applied in combination with an acoustically active agent (e.g., microbubbles). Furthermore, it should be noted that the ultrasound may be applied continuously over an extended period of time (e.g., several hours). Similar to the previously described embodiment, the pulse width of an ultrasound beam transmitted by the ultrasound probes described above can be short (e.g., 10 µs-1000 µs) in combination with a duty cycle between, e.g., 1-50%. The acoustic output power may be chosen to accomplish a focal maximum intensity below the FDA-suggested limit of 720 mW/cm$^2$.

The application of noninvasive ultrasound either alone, or in combination with intravenously administered acoustically active agent such as microbubbles, can be performed with ultrasound transducers and a power and control device/module that can be relatively small, preferably pocket-sized. The power and control device may be battery charged to allow for portable and/or wireless functionality. Additionally still, the power and control device can have a substantially easy-to-use user interface, as well as being durable and waterproof. Other features and/or functionalities may be incorporated into one or more designs of the control device as, e.g., dictated by the environment(s) in which the device may be utilized. In accordance with one embodiment, the power and control device may be provided with an on/off switch, not more than two control buttons, and a main control display. Such control buttons may include, but are not limited to the following: an automated adjustment of acoustic output power ("Automated PCD Control") button, where PCD can refer to Passive Cavitation Detection; and a manual adjustment of acoustic power ("Manual PCD Control") button. It should be noted that in accordance with certain embodiments, manual adjustment of acoustic power may involve selection of one of a plurality of output power ranges that can depend on one or more, but not necessarily limited to the following: patient age group, e.g., a) <20, b) 20-40, b) 41-60, c) 61-75, d) >76 years of age; gender, e.g., a) Female, b) Male; and race, e.g., a) Caucasian, b) Hispanic, c) Asian, d) African/African-American. Additionally, the power and control device may include one or more lights, such as light emitting diode (LED) lights, for example, to present cavitation control and upper power limit indications (e.g., yellow, green, and red) to a user.

Similar to electrocardiography (ECG) pads, the power and control device may utilize disposable ultrasound transducers which can be connected to the power and control device via some type of wired connection, and which can be discarded after use. The ultrasound transducers, as described above, can be placed onto the temporal bone area on both sides of a patient's head. The ultrasound transducer can be held in place using a gel-like temporary glue, such as that used for ECG pads, for example, as will be described in greater detail below. To provide sufficient conductivity between the ultrasound transducers and the patient's skin, hair may be removed at the location where the ultrasound transducers are applied. After the ultrasound transducers have been positioned, the power and control device can be powered on using the on/off switch. As described above, lights can be used in the control device to present certain indications to a user. For example, a yellow control light can be used to provide visual confirmation to the user that the control device is operative, e.g., transmitting sound waves (i.e., ultrasound beams). It should be noted that a default acoustic output power value can be set after turning the control device on, which can be in the milliWatts range (e.g., 20 mW).

Subsequent to powering on the power and control device, options may be provided to the user via, e.g., the main control display. A first option may be effectuated if the user chooses to press the Automated PCD Control button, where the power and control device can automatically increase the acoustic output power until the green control light illuminates. This green control light can be used as confirmation of the occurrence of stable cavitation of microbubbles. Stable cavitation is suggested as the underlying mechanism to trigger the biophysical effects mentioned above. Therefore, illumination of the green control light may represent the intended therapeutic activity or, in other words, the "therapeutic window." A red control light can indicate that this therapeutic window has been exceeded, for example. In this case, the acoustic output power will be decreased automatically until the red control light turns off and the green control light turns on.

A second option can be effectuated if the user chooses to press the Manual PCD Control button, where the power and control device can allow the user to increase the acoustic output power manually. As described above, manual acoustic output power can be chosen/adjusted up or down depending on one or more factors, e.g., the patient's age, sex, and/or race. During manual control, the user may, e.g., increase the acoustic output power and utilize the green control light as a gauge, where the green control light (as previously discussed) can indicate operation of the power and control device in a "proper" therapeutic window. If the acoustic output power is exceeded using the Manual PCD Control function, the power and control device can either shut down or switch back to a default setting (i.e., that indicated by a yellow control light as described previously).

The power and control device can further drive the ultrasound transducers, where power can be supplied by, e.g., a lithium polymer (LiPo) or similar battery (which can also power the aforementioned features and/or functionality of the power and control device). A power conversion control circuit can produce a desired ultrasound frequency. Another circuit of the power and control device can be used to control the output power level, which can consider input provided by a user pertaining to the patient, e.g., gender, race, and age. Still another circuit can be used to modulate the output frequency in such a way that intracranial ultrasound standing waves are prevented from occurring. Yet another circuit can be used to sense whether the ultrasound transducers are connected, functional, and/or energized.

As alluded to previously, the power and control device can be relatively small, for example, pocket/hand-held sized, and made of one or more materials that can withstand, e.g., hard use in environments like that experienced in an emergency response vehicle/scenarios in which an emergency response vehicle is needed. For example, the power and control device may be approximately the size of a hand-held digital multimeter, e.g., approximately 2×4×8 inches. Although, as described above, the battery can be rechargeable (e.g., a lithium polymer batter), it should be noted that the power and control device may alternatively, or additionally, have the ability to be operated directly from a stationary power source, such as a wall outlet. Additionally, the power and control device can be configured such that the battery is easily replaceable.

Also as previously alluded to, the power and control device may have one or more buttons, user interfaces, etc. that can allow a user to interact with the power and control device. Accordingly, the power and control device can have a control panel through which those various buttons and user interfaces can be implemented and/or presented for interaction, e.g., turning the device on/off; verifying that the ultrasound transducers are energized when appropriate; ascertaining how much battery life is left, automated adjustment of acoustic output power, and manual adjustment of acoustic power. Further, the power and control device may include, as part of the control panel or separate therefrom, the aforementioned control lights indicative of, e.g., cavitation control and upper power limit. The power and control device can further include one or more connector receptacles. A first connector receptacle may be configured for recharging the battery and/or operation from a wall outlet, while a second connector receptacle may be configured to receive a cable for connecting the ultrasound transducers to the power and control device.

A transmit signal can be generated by the power and control device using an oscillator circuit tuned to, e.g., a nominal 200 kHz continuous sine wave. The sine wave can be amplified to an appropriate power level, and this transmit signal can be applied to a switching circuit that alternates transmission between two sets of leads (one per ultrasound transducer), for example, every 100 μs, in a case where the ultrasound transducers are positioned at the temporal bone on both sides of a patient's head. This transmit signal can be applied to the ultrasound transducers that have been positioned and secured to the head of the stroke patient via aforementioned cable. The switching circuit can create, for example, a 100 μs on-time followed by a 100 μs off-time for each ultrasound transducer, such that when one ultrasound transducer is in the on state, the other ultrasound transducer is in the off state. During the ultrasound transducer on state, the ultrasound transducer can transmit ultrasound energy through the patient's skull. During the ultrasound transducer off state, the ultrasound transducer can receive acoustic signals allowing it to be utilized as a passive cavitation detector, when ultrasound is applied in conjunction with an acoustically active agent.

Additionally still, the power and control device can include, e.g., two switches or actuators, although more or less switches may be included depending on need/desired level of control of operation. A first switch may be used to turn the power and control device on, and a second switch may be used to send the aforementioned transmit signal/voltage to the ultrasound transducers. Moreover, an input device such as a touchpad may be used to input patient information or further interact with the power and control device. When the ultrasound transducers are connected, but before they are energized, an indication that the ultrasound e transducer is connected and functional can be presented to a user. This may be a light or a message on the touchpad, for example. When the required preliminary conditions have been met (e.g., patient information, transducer functionality, etc.) then the user may energize the ultrasound transducers, and when this is done, an indicator can also show this condition.

Figure 4:
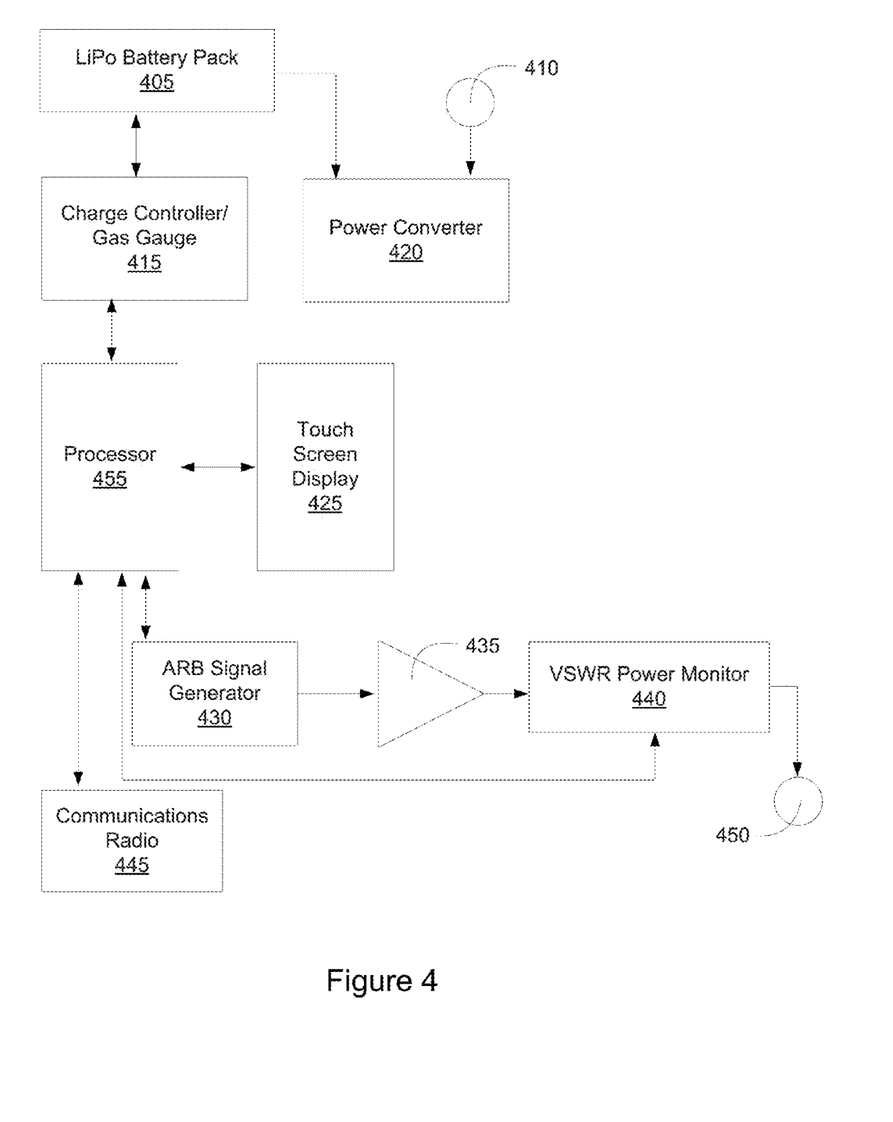
FIG. 4 is a schematic representation of the power and control module of FIG. 3.

FIG. 4 illustrates an example schematic diagram of a power and control device 400 designed in accordance with various embodiments. The power and control device 400 may be powered by a battery power source, such as LiPo battery pack 405. Charging of the LiPo battery pack 405 can be performed by a direct current (DC) charging port 410. Additionally, the power and control device can be powered from, e.g., a wall outlet, via the DC charging port 410. The power and control device 400 can include a charger controller and gas gauge 415 (e.g., a BQ series charge controller/gas gauge) for monitoring cavitation as described in greater detail below, as well as a power converter 420. Further still, the power and control device 400 may have a touch screen display 425, such as an organic light emitting diode (OLED) touch screen display through which a user may be presented with various information/interact with the power and control device 400. As well, the power and control device 400 may include a signal generator 430, such as an arbitrary waveform generator (ARB) signal generator, a power amplifier 435, and a voltage standing wave ratio (VSWR) power monitor 440 for the generation/control/transmission of ultrasound as described herein. The power and control device 400 may also include one or more communications radio modules 445, which may be, e.g., a Bluetooth® radio, through which the aforementioned wireless communications can be effectuated. To allow connection of the ultrasound transducers to the power and control device 400, a probe connector(s) 450 may also be provided on the power and control device 400. Moreover, operation of the various functionality of the power and control device 400 described herein can be performed by a processor 455, which may be, e.g., an ARM3 core processor, or a combination of processors/controllers. It should be noted that more or less elements/modules/components can be included in the power and control device 400 in accordance with desired features and/or functionality. Moreover, the various elements/modules described herein can implemented as separate elements/modules, or combinations thereof.

As indicated previously, the therapeutic approach described herein can be based on the application of ultrasound either alone or in conjunction with an acoustically active agent, such as microbubbles, which relies on a stable cavitation mechanism. Furthermore, the utilization of the acoustically active agent, e.g., microbubbles, allows for the monitoring function described herein to be achieved. It should be noted that the term "microbubbles" can refer to an agent designed for diagnostic purposes to enhance image quality. It should be noted that as utilized herein, the term microbubbles is not meant to be restricted to merely their diagnostic application. Rather, and in accordance with various embodiments, the microbubble concept may additionally be applicable to agents not primarily designed for diagnostic purposes.

That is, diagnostic microbubbles can refer to spheres with an average diameter of, e.g., 2-3 µm. The shell structure of such spheres or microbubbles can be either a phospholipid or human albumin, whereas the inside of such spheres may be filled with a perfluorocarbon gas. The agents can be administered, in accordance with various embodiments intravenously, e.g., via a peripheral vein, and are stabilized to pass through the lungs to enter arterial circulation. The half-life of such agents may be within the range of minutes.

When ultrasound waves are transmitted through a physical medium, the ultrasound waves can compress and stretch the molecular spacing of the physical medium, such as human tissue. Accordingly, and when a microbubble passes an ultrasound field it undergoes frequent pressure changes, leading to either bubble oscillation (i.e., stable cavitation) or bubble destruction (i.e., inertial cavitation). Whereas inertial cavitation might cause harm to human tissue, specifically the endothelial layer, stable cavitation has been shown to be effective with respect to clot lysis and improvement of tissue perfusion, stable cavitation occurs at lower ultrasound energies.

Referring back to the control lights implemented in the power and control device, a green control light can be illuminated when the therapeutic window has been reached, i.e., when stable cavitation can be detected. As inertial cavitation can require higher energies to occur, inertial cavitation may occur predominantly when energies might be increased beyond the therapeutic window. In this case, a red control light can be illuminated.

Referring back to the ultrasound transducers utilized for transmitting ultrasound, and to provide control over cavitation, the ultrasound transducers may be designed such that they are capable of detecting cavitation signals whenever they are not transmitting (e.g., in an off phase). The ultrasound transducers can further be designed to cover a bandwidth of, e.g., 100-300 kHz to capture a subharmonic frequency (0.5× transmit frequency: 0.5×200 kHz=100 kHz), as well as a first ultraharmonic frequency (1.5× transmit frequency: 1.5×200 kHz=300 kHz). Given this capability, cavitation can be detected and characterized by the device as being one of stable or inertial cavitation.

It should be noted that after the ultrasound transducers are in place on a patient's head, the intravenous infusion with microbubbles has been initiated, and the preferred or optimal acoustic output power has been chosen, it is contemplated that continuous insonation (application of ultrasound) be started at the earliest point possible, i.e., after first aid has been administered and the patient's vital functions have been stabilized. This could be either at the site of the emergency or during patient transport to a care facility. Furthermore, continuous insonation may last until further in-hospital diagnostic or therapeutic procedures are provided, the patient's symptoms are fully resolved, the patient's symptoms have worsened, and/or at any given point in time, a care-taking physician recognizes a significant medical indication to discontinue such treatment.

As described above, the ultrasound transducers can be positioned onto a patient's head via gel-pads using, e.g., a conductive gel, similar to that utilized for affixing ECG electrodes to a patient's chest wall. The ultrasound transducers may be positioned on either side of the patient's head, over the temporal bone region forward of the ears, or alternatively, on the very top of the head (vertex). The latter, alternative positioning may be preferable in certain scenarios as this transskull pathway may have advantages due to its specific acoustic properties.

Again, it is preferred that the ultrasound transducers are designed for a single-use application, and packaged so as to maintain sterility until use, although the ultrasound transducers can be designed for multiple-use applications as well. The transducer/gel-pad combination, being pliant, can conform to the shape of a patient's head/skull, and can aid in the transmission of the ultrasound energy/waves into a target region of the patient's brain. The conductive gel can have acoustic properties similar to, e.g., coupling gels used in ultrasonography. The portion of the gel-pad that contacts the patient's scalp may have a peel-away strip that will expose a layer of adhesive that can help keep the ultrasound transducer in place, and also aid in the transmission of ultrasound energy/waves by helping to eliminate potential air pockets, for instance, due to a patient's hair. Optionally, as previously indicated, shaving of the ultrasound transducer application area may be considered.

An ultrasound transducer itself can be contained in the gel-pad portion. The transducer can include a piezo-electric element (e.g., disc-shaped), approximately 3 cm in diameter and 2 mm thick. The piezo-electric material can be a material used for medical ultrasound, such as lead zirconate titanate (PZT), or any other suitable material. The piezo-electric material, also referred to as the crystal, can have both faces, but not necessarily the edge, coated with an electricity-conducting material, which can be referred to as the electrodes of the ultrasound transducer. The crystal may further have an insulating coating, over which a shield layer is applied. Wire leads, such as lightweight and flexible cable (twisted, shielded pair) can be attached (e.g., soldered) to the electrodes for the purpose of conducting electricity to the crystal, and the subsequent generation of ultrasound energy. It should be noted that other materials may be used for additional coatings as required, such as a quarter-wave matching layer on a side of the crystal nearest the patient to aid in energy transmission, a backing layer on the side of the crystal away from the patient, a shielding layer to prevent electro-magnetic interference (EMI), and/or another insulating coating to prevent inadvertent shocking of the patient.

Designed for single use, as described above, the ultrasound transducers need not require any housing material or special connectors. Rather, the ultrasound transducers can be integrated into, e.g., a low-profile and lightweight plastic bag that has dimensions slightly larger than the ultrasound transducers themselves. One side of the plastic bag may contain a dispenser for the adhesive coupling gel, and another side may have an air pocket to provide air-backing for the ultrasound transducers. Such a package can be sealed within a disposable envelope or similar enclosure to maintain sterility. Upon use, the disposable envelope can be opened and an ultrasound transducer removed. An additional membrane/peel-away strip can be removed from one side of the ultrasound transducer to expose the adhesive and coupling gel, and the ultrasound transducer may be applied to a selected area on a patient's head.

The ultrasound transducers can fit inside the gel-pads in such a way that some thickness of gel can be maintained between the energy-emitting face of the ultrasound transducer and the patient's scalp. This may be accomplished for instance, by incorporating a sleeve in the gel pad into which the ultrasound transducer can be inserted during the manufacturing process. The electrode leads of the ultrasound transducer can exit the gel-pad in such a way that they are secured against inadvertent snagging and breakage during emergency deployment. A cable can be used to connect the electrode leads to the aforementioned power and control device.

It should be noted that in accordance with another embodiment, the ultrasound transducers can be implemented in a headband, where the electrode leads can exit the gel-pad portions of the headband, and may be incorporated into the headband material to secure against inadvertent snagging and breakage during emergency deployment. The leads from each of the ultrasound transducers may terminate at a convenient portion of the headband, such as the portion positioned over the back of the head. This termination may be a connector built into the headband, or may be a length of cable that terminates in a connector. Another cable, separate from the headband, can be used to connect the headband to the power and control device.

Figure 3:
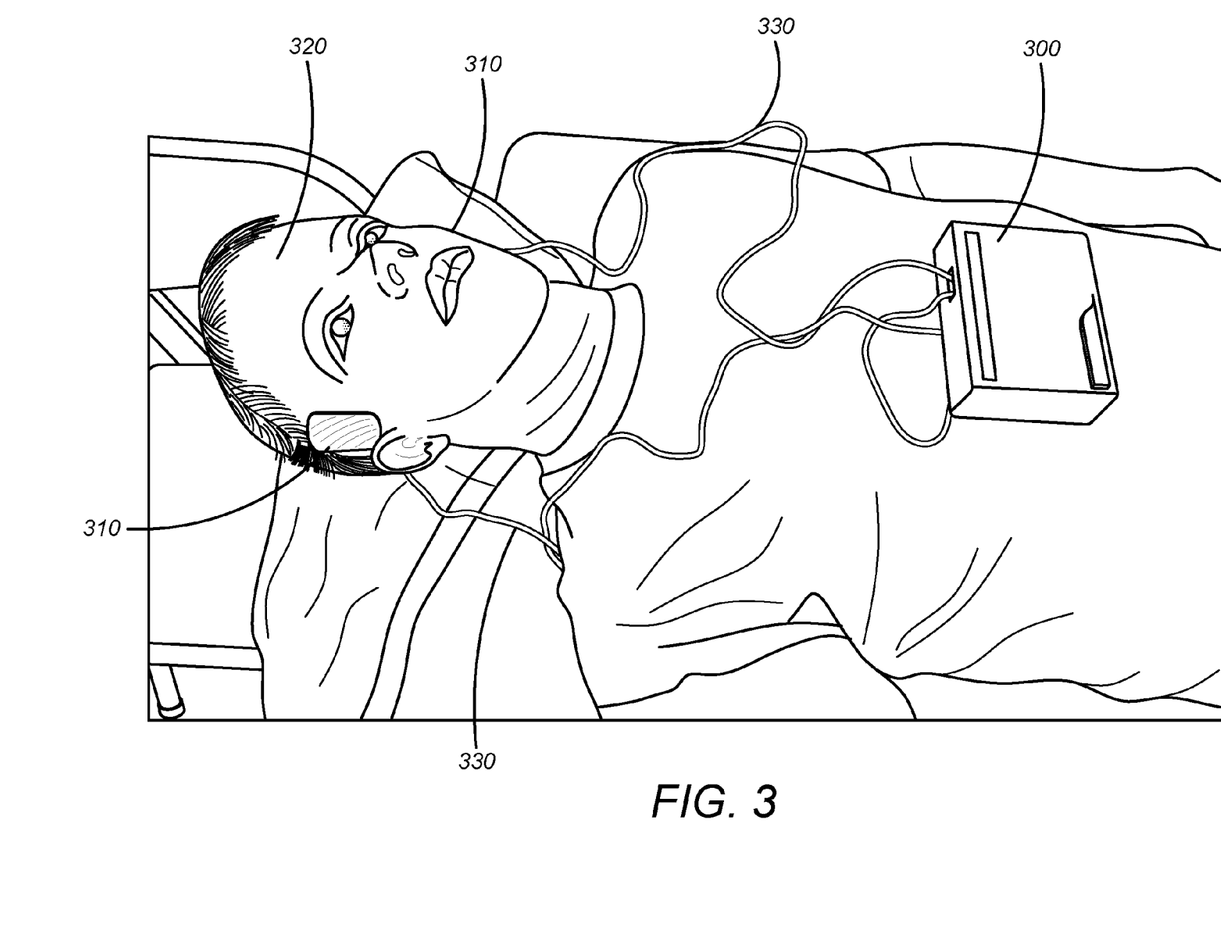
FIG. 3 illustrates an example implementation of a power and control module configured and utilized in accordance with various embodiments for in-field treatment of a stroke victim.

FIG. 3 illustrates an example configuration of the ultrasound transducers and power and control device, as well as the use thereof. FIG. 3 illustrates a power and control device 300. As previously described, the power and control device can be relatively small, battery powered, and have wireless communication functionality, and can power and control ultrasound transducers. Connected to the power and control device are ultrasound transducers 310 shown as being attached to the head of a patient 320. Again, the ultrasound transducers 310 can be connected to either side of the head of the patient 320 via a gel-pad. The ultrasound transducers, including ultrasound transducer 310 may be connected to the power and control unit via cables 330.

The ultrasound transducers themselves may be designed to operate at a frequency of 200 kHz, or in a band of frequencies centered about 200 kHz. Again, the acoustic field at such frequencies is not necessarily subject to distortion when passing through the skull, as is the case with higher frequencies in the MHz range. As a result, the acoustic field that is applied to the brain may be designed according to known physical principles with a high degree of predictability. Additionally, the ultrasound transducers can be configured as, e.g., flat unfocused disks with a diameter between, e.g., 2 cm and 3 cm, resulting in a radius of, e.g., 1 cm and 1.5 cm, respectively.

In acoustic terms, the radius of an ultrasound transducer is typically represented as a. The acoustic field emanating from such an ultrasound transducer is essentially columnar until it travels a distance d, when it begins to spread in a conical fashion. The distance d is also known as the far-field transition, and can be represented by the following equation:

$$d = \frac{a^2}{\lambda}$$

where $\lambda$ is the wavelength of the ultrasound wave. In water and body tissue at 200 kHz, $\lambda$ can be approximately 0.75 cm. Hence, and for an ultrasound transducer with a radius of, e.g., 1 cm, the distance d is approximately 1.3 cm, and for a radius of 1.5 cm, the distance d is 3 cm.

Past distance d, the acoustic energy of an ultrasound wave can spread in a conical shape that is subtended by an angle $\theta$, the angle between the acoustic axis and one side of the conical shape. This angle $\theta$ may be calculated by the following equation:

$$\theta = \tan^{-1}\left(\frac{a}{d}\right)$$

It can be seen from these equations that for a given ultrasound frequency, the acoustic beam shape is primarily controlled by the radius of the ultrasound transducer. Beam shape in turn, can determine the peak intensity of the acoustic field. As the radius of the beam expands according to the angle $\theta$, the beam intensity decreases as the square of the radius. The beam intensity can also decrease with distance due to attenuation by the brain tissue. Such effects can be a factor regarding the safety and possibility of creating standing waves (discussed in greater detail below) in the cranial region of a patient.

The following example illustrates the design, operation and inherent safety of various embodiments. An ultrasound transducer of radius 1.5 cm has a transition distance of 3 cm, which can be the point of peak acoustic intensity, inasmuch as beyond this distance, the beam transmitted by the ultrasound transducer becomes wider. If the acoustic output power of the ultrasound transducer has been adjusted to produce, e.g., 600 mW/cm$^2$ acoustic intensity at this point of peak acoustic intensity, at a 5 cm depth, the acoustic intensity can drop off to less than 300 mW/cm$^2$, and at 6 cm, the acoustic intensity can drop off to approximately 125 mW/cm$^2$. Given an average skull diameter of 16 cm, the acoustic intensity of the beam can be on the order of 20 mW/cm$^2$ by the time it reaches the opposite skull surface. Any standing waves generated by reflection at the contralateral interior skull surface should be of negligible amplitude. And yet, the intensity of the ultrasound energy that is most likely to have a therapeutic effect is contained in the clinically relevant depth of 30-60 cm on the ipsilateral side of the brain midline.

Further to the above, a pulse duration of between 10-10000 μs may be contemplated, with a 1-50% duty cycle, at a frequency of 200 kHz (a convenient paradigm in another sense because the wavelength for this frequency is approximately 7.5 mm in soft tissue). A 20-cycle burst, given, for example, a pulse duration of 100 µs, and a duty cycle of 50%, would be 15 cm in total length, or nearly the diameter of the average cranium from one temporal bone to the other. If the two ultrasound transducers alternate active times, previously referred to as on-time, the acoustic field of a first ultrasound transducer would be much diminished by the time the energy of the second ultrasound transducer passes through, thus minimizing any likelihood of creating standing waves. As described above, to provide this alternating activity, the power and control device may utilize a switching circuit to switch, e.g., a 200 kHz CW signal from one set of conductors to another set every 100 µs to create alternating 20 cycle bursts between the ultrasound transducers. It should be noted that the same or similar considerations are applicable in an embodiment where a single ultrasound transducer is utilized and positioned at the vertex of a patient's head.

Regarding the application of an acoustically active agent in accordance with one embodiment, and as described above, the ultrasound transducers have the capability to receive acoustic signals during an off-time. Relying on stable cavitation as the underlying mechanism to achieve the aforementioned biophysical effects, and relying on inertial cavitation used as a control and safety measure, the ultrasound transducers may have a minimum bandwidth between 100-300 kHz. This range has been chosen, as also described above, to capture the subharmonic frequency (100 kHz) as well as the ultraharmonic frequency (300 kHz). The occurrence of both frequencies indicates the presence of stable cavitation, and therefore, describes the individual therapeutic window. The occurrence of primary inertial cavitation may be characterized by a combination of an increased area under the curve of the fundamental frequency (at 200 kHz) and a raise of the noise floor. Sub and ultra-harmonic frequencies may still be present, but are not dominant. Should inertial cavitation be detected by the ultrasound transducers, the power and control device can be configured to automatically lower acoustic output until only stable cavitation can be detected (i.e., the Automated PCD Control button). Alternatively, the power and control device can be configured to shut down instantaneously or automatically reset to its preset mode (i.e., the Manual PCD Control button).

Figure 6:
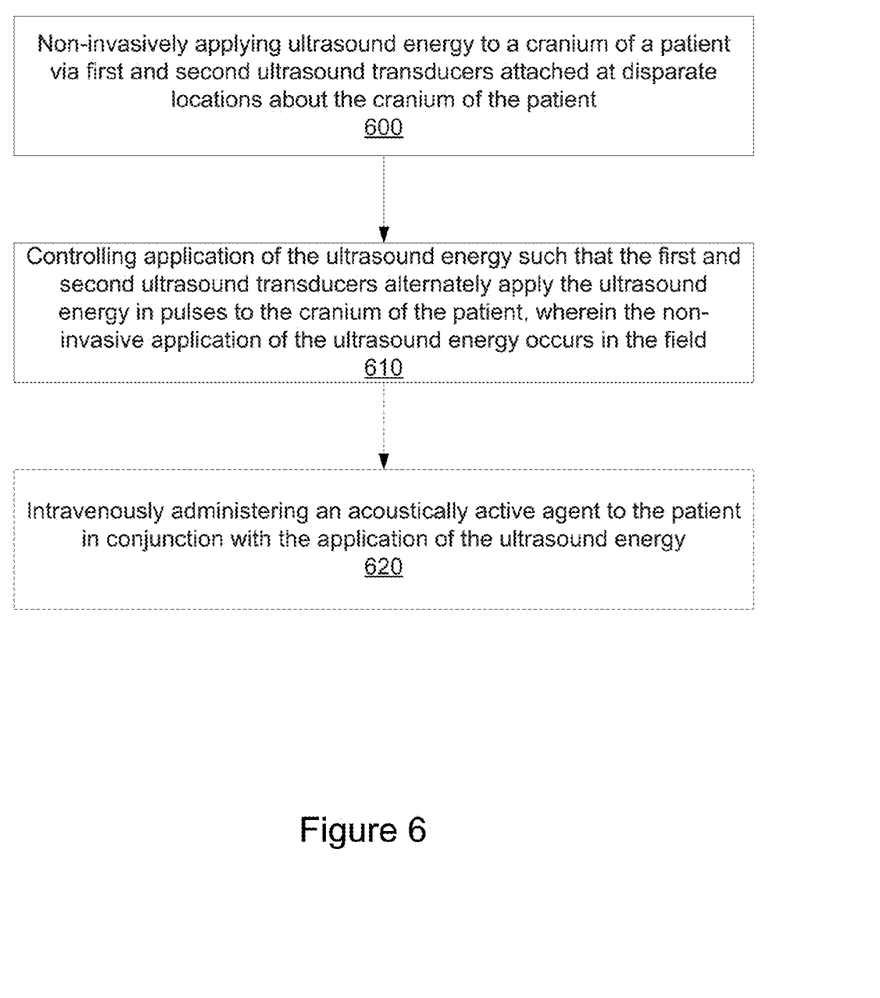
FIG. 6 illustrates example processes performed for treating stroke victims in the field in accordance with various embodiments.

FIG. 6 illustrates example processes performed to treat victims of stroke or stroke-like events in the field in accordance with various embodiments. At 600, ultrasound energy is non-invasively applied to a cranium of a patient via first and second ultrasound transducers attached as disparate locations about the cranium of the patient. At 610, application of the ultrasound energy is controlled such that the first and second ultrasound transducers alternately apply the ultrasound energy in pulses to the cranium of the patient, wherein the non-invasive application of the ultrasound energy occurs in the field. Optionally, at 620, the application of the ultrasound energy can be performed in conjunction with intravenously administering an acoustically active agent to the patient. For example, and as described herein, the administration of, e.g., microbubbles, and stable cavitation caused by the application of ultrasound energy at particular levels can promote lysis, restoration of arterial flow, etc.

Additionally, the design of the ultrasound transducers in accordance with various embodiments can provide a guaranteed minimum half-life of 24 hours. For subacute/chronic applications, the requirements for the ultrasound transducers half-life might be different in the sense of longer term durability, assuming proper care and maintenance in a controlled environment (e.g., hospital, rehabilitation center, or retirement home).

Regarding macrocirculation, there is evidence that ultrasound-induced clot lysis to recanalize a vessel can be improved in combinational use with ultrasound microbubbles. Thus, and in accordance with still another embodiment, ultrasound sequences can be built into the power and control device for the use of microbubbles during ultrasound exposure. The microbubble compounds used for this purpose can be standard, commercially available agents which are primarily used for diagnostic purposes or agents which are specifically developed for the purpose of ultrasound enhanced clot lysis.

As to microcirculation, there is growing evidence that ultrasound in combination with microbubbles may induce the release of nitric oxide from endothelial cells, resulting in a vasodilatative effect, which in turn can result in improved tissue perfusion. In accordance with another embodiment, microcirculation techniques can be incorporated into the various embodiments previously described to improve the tissue perfusion through mechanical and biochemical vasodilatation.

It should be noted that the various embodiments disclosed herein for treating stroke victims are also applicable to other ischemic diseases caused by embolic or thrombo-embolic events, such as myocardial infarction (MI) or deep vein thrombosis (DVT). That is, the underlying cause for all these diseases is the sudden occlusion of a vessel by a blood clot with the consequence of consecutive cell death in the supplied area due to lack of oxygen supply. All of these diseases have in common, the acuity of onset and the need for a therapeutic option at the earliest time point possible. Hence, a treatment which could be provided at the site of emergency and/or during transport to a care facility would be advantageous. Accordingly, various embodiments can include alternative ultrasound transducer designs, as well as ultrasound sequences, that may be dedicated for application to other ischemic diseases, such as MI or DVT. Moreover, various embodiments may be utilized to address ischemic diseases in almost any organ system.

Further still, and beyond application in acute ischemic diseases, various embodiments disclosed herein may also be used as a long-term, recurrent treatment option, for example, in patients suffering from subacute/chronic ischemic diseases. Such patients may include those with chronic ischemic white matter disease, patients suffering from vascular dementia or post stroke patients. In these patient populations, various embodiments could be utilized, for example, during hospitalization, during rehabilitation, or as a regular treatment at private homes or in retirement facilities. The use of various embodiments may further be utilized in the context of neurodegenerative diseases, such as Alzheimer's or Parkinson's disease, following a similar approach. That is, various embodiments disclosed herein are contemplated for use in the treatment of any subacute or chronic brain-diseased patients for whom improved tissue perfusion, the potential stimulation of stem cell proliferation, neuromodulation or the induction of chaperone protein release could be beneficial. Various embodiments may also be utilized in various neurological applications, e.g., the treatment of seizures or neuropsychiatric diseases (e.g. schizophrenia, depression).

Other embodiments may include monitoring or feedback functionality at the power and control device, for example, to establish, e.g., the time of vessel recanalization or improvement of tissue perfusion. Still other embodiments may include one or more sensing elements into the transducer/gel-pad combination, such as infrared lasers or cavitation receivers, to monitor, e.g., the improvement of tissue perfusion during the procedure, or to prevent exceeding safety limits by cavitation detection.

As alluded to above, the power and control device may have wireless functionality. Such wireless functionality may encompass wireless communication between, e.g., paramedic teams in the field and medical personal in a receiving care facility, where such communications have conventionally been sparse. Still other embodiments may utilize the wireless communication capabilities for the transmission of real-time data from the power and control device (e.g., data regarding/associated with the aforementioned monitoring/feedback functionality) directly to an allocated server at the receiving care facility, or to a portable computing device using a variety of wireless communication technologies, including for example, but not limited to 2G (e.g., Global System for Mobile Communications (GSM), etc.), 2.5G (e.g., General Packet Radio Service (GPRS), etc.), 3G (e.g., Enhanced Data for GSM Evolution (EDGE), Wideband Code Division Multiple Access (WDMA), CDMA2000, etc.), and 4G (e.g., LTE, WiMAX, etc.) technologies, and Bluetooth®.

Further still, the functionality disclosed herein and described as being implemented utilizing ultrasound transducers connectable to and powered by a power and control device can be implemented in existing devices, such as existing diagnostic ultrasound devices. Moreover, recent research in the field of local drug delivery involves the delivery of therapeutic agents at a target site. In particular, certain research suggests using microbubbles as transport vehicles, and ultrasound as a source to release these therapeutic agents at the target site. For example, certain research has been focused on the beneficial effect of oxygen carriers for tissue preservation and neuroprotection. Accordingly, various embodiments may implement dedicated ultrasound sequences allowing the methods and apparatuses disclosed herein for the delivery of drugs locally, or to enhance the effect of oxygen carriers.

As described herein, various embodiments provide methods and apparatuses to initiate stroke treatment in the field and/or during the transport of a patient to a care facility, as well as for other diseases, and for more prolonged use, such as in rehabilitation scenarios. Various embodiments may be adjusted, e.g., automatically, to an individual "therapeutic window" for each patient, often a crucial factor due to significant differences in skull morphology between humans of different age, gender, and/or race. Further, various embodiments can be utilized for ultrasound transmission in combination with the use of acoustically active agents, such as microbubbles, where stable cavitation is an underlying mechanism for both the therapeutic application as well as its control.

Figure 5:
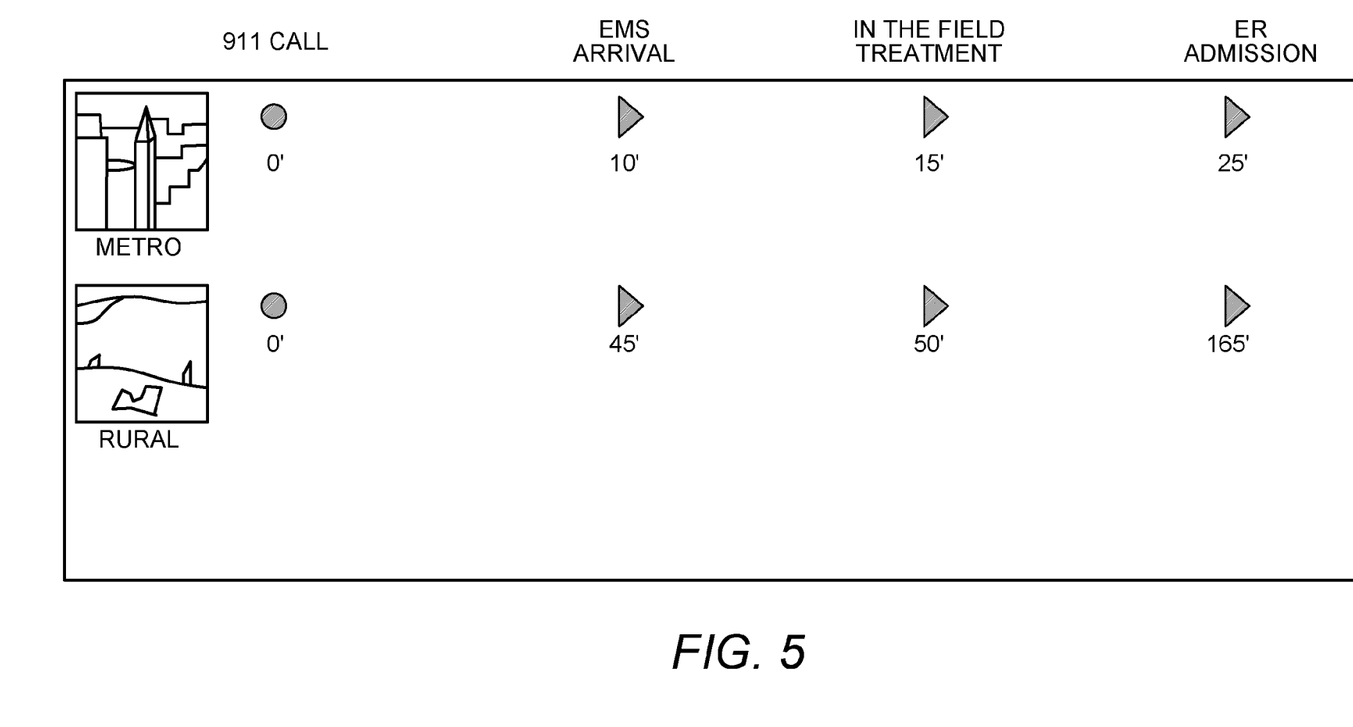
FIG. 5 is an illustration of time delay effects and possible tissue damage reduction upon use of various embodiments.

Accordingly, the millions of patients who suffer from acute stroke-like syndromes can be treated, worldwide, for whom therapeutic options to-date do not exist. Additionally still, use of this approach can be incorporated into a future Standard of Care for the treatment of acute stroke in the field, much like the defibrillator has become the Standard of Care for cardioconversion. The potential for reduction in delays experienced in the treatment of acute stroke in both rural and metropolitan areas is significant, as illustrated in FIG. 5. In a metropolitan area, for example, an emergency 911 call may be received, and 10 minutes may pass until emergency medical services (EMS) personnel arrive at the site where a patient has experienced a stroke/stroke-like event. Application of ultrasound/ultrasound in conjunction with microbubbles, for example, in accordance with various embodiments can be accomplished in the field within, e.g., 5 minutes thereafter. Admission to a care facility may occur 10 minutes after that. Hence, in this example, at least 10 minutes can be saved during which a dramatic reduction in tissue damage can be effectuated. In a rural environment, arrival of EMS personnel may not occur until 45 minutes after an initial emergency 911 call. Again, within 5 minutes, the application of ultrasound alone or in conjunction with microbubbles can occur in accordance with various embodiments. In such a rural scenario, admission to a care facility may not occur for another 115 minutes thereafter. In this instance, it can be appreciated that 115 minutes during which tissue damage due to stroke can be avoided through the utilization of various embodiments.

The various diagrams illustrating various embodiments may depict an example architectural or other configuration for the various embodiments, which is done to aid in understanding the features and functionality that can be included in those embodiments. The present disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement various embodiments. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

It should be understood that the various features, aspects and/or functionality described in one or more of the individual embodiments are not limited in their applicability to the particular embodiment with which they are described, but instead can be applied, alone or in various combinations, to one or more of the other embodiments, whether or not such embodiments are described and whether or not such features, aspects and/or functionality is presented as being a part of a described embodiment. Thus, the breadth and scope of the present disclosure should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

Moreover, various embodiments described herein may be described in the general context of method steps or processes, which may be implemented in one embodiment by a computer program product, embodied in, e.g., a non-transitory computer-readable memory, including computer-executable instructions, such as program code, executed by computers in networked environments. A computer-readable memory may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

As used herein, the term module can describe a given unit of functionality that can be performed in accordance with one or more embodiments. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality. Where components or modules of the invention are implemented in whole or in part using software, in one embodiment, these software elements can be implemented to operate with a computing or processing module capable of carrying out the functionality described with respect thereto. The presence of broadening words and phrases such as "one or more," "at least," "but not limited to" or other like phrases in some instances shall not be read to mean that the narrower case is intended or required in instances where such broadening phrases may be absent.

What is claimed is:

1. A method, comprising:
   non-invasively applying ultrasound energy to a cranium of a patient via first and second ultrasound transducers attached at disparate locations about the cranium of the patient;
   intravenously administering an acoustically active agent to the patient;
   exciting the acoustically active agent by the ultrasound energy to cause stable cavitation, controlling application of the ultrasound energy such that the first and second ultrasound transducers alternately apply the ultrasound energy in pulses to the cranium of the patient;
   during a time in which either the first or second ultrasound transducer is not applying ultrasound energy, detecting a state of cavitation of the acoustically active agent using the respective first or second ultrasound transducer, determining a type of cavitation from the detected state, and
   if the type of cavitation is inertial, whereby the application of the ultrasound energy has exceeded a level commensurate with a therapeutic window, then reducing an output power of the ultrasound energy until stable cavitation is detected; and
   if the type of cavitation is stable, then maintaining the output power of the ultrasound energy such that stable cavitation is maintained;
   wherein the non-invasive application of the ultrasound energy occurs at the site of an emergency and/or during transport to a care facility.

2. The method of claim 1, wherein the disparate locations about the cranium of the patient comprise temporal bone regions forward of the ears of the patient.

3. The method of claim 1, wherein the acoustically active agent comprises microbubbles.

4. The method of claim 1, wherein the stable cavitation triggers a plurality of biophysical effects in the patient.

5. The method of claim 4, wherein the controlling of the application of the ultrasound energy is performed automatically.

6. The method of claim 5, wherein performing the automatic control further comprises automatically controlling the application of the ultrasound energy in accordance with at least one of patient-specific characteristics.

7. The method of claim 6, wherein the at least one of the patient-specific characteristics comprises at least one of age, gender, race, skull bone characteristics, and morphology.

8. The method of claim 1, further comprising, performing the non-invasive application of the ultrasound energy and the controlling of the application of the ultrasound energy to counteract effects of at least one of myocardial infarction, deep vein thrombosis, and a cerebrovascular accident due to ischemia.

9. The method of claim 1, wherein each of the first and second ultrasound transducers are connected via cables to a portable, battery-operated power and control device, and wherein the first and second ultrasound transducers comprise single-use ultrasound transducers.

10. The method of claim 9, wherein the first and second ultrasound transducer comprise single-use ultrasound transducers comprising disk-shaped piezo-electric elements.

11. The method of claim 9, wherein the first and second ultrasound transducers comprise single-use ultrasound transducers, wherein the single-use ultrasound transducers transmit at either a frequency of 200 kHz or in a band of frequencies centered about 200 kHz, and wherein the single-use ultrasound transducers receive acoustic signals in a minimum bandwidth between 100 to 300 kHz.

* * * * *